(12) United States Patent
Mäentausta et al.

(10) Patent No.: US 9,081,000 B2
(45) Date of Patent: Jul. 14, 2015

(54) CARTRIDGE FOR BODY FLUID MEASURING STRIPS AND A BODY FLUID MEASUREMENT DEVICE

(75) Inventors: Jarmo Mäentausta, Espoo (FI); Jukka Planman, Espoo (FI); Tuomas Planman, Espoo (FI)

(73) Assignee: Mendor Oy, Espoo (FI)

( * ) Notice: Subject to any disclaimer, the term of this patent is extended or adjusted under 35 U.S.C. 154(b) by 542 days.

(21) Appl. No.: 13/375,503

(22) PCT Filed: Jun. 7, 2010

(86) PCT No.: PCT/FI2010/050465
§ 371 (c)(1),
(2), (4) Date: Feb. 14, 2012

(87) PCT Pub. No.: WO2010/139864
PCT Pub. Date: Dec. 9, 2010

(65) Prior Publication Data
US 2012/0125086 A1 May 24, 2012

(30) Foreign Application Priority Data
Jun. 5, 2009 (FI) .................................. 20095628

(51) Int. Cl.
*G01N 33/49* (2006.01)
*G01N 33/487* (2006.01)

(52) U.S. Cl.
CPC ...... *G01N 33/48757* (2013.01); *G01N 33/4875* (2013.01); *G01N 33/48778* (2013.01); *G01N 33/49* (2013.01)

(58) Field of Classification Search
CPC .............. G01N 35/00; G01N 33/4875; G01N 33/48757; G01N 33/48778; G01N 33/49
See application file for complete search history.

(56) References Cited

U.S. PATENT DOCUMENTS 8,282,578 B2 * 10/2012 Rush et al. ..................... 600/584
2004/0178216 A1 * 9/2004 Brickwood et al. .......... 221/268
(Continued)

FOREIGN PATENT DOCUMENTS

CA   2583563     *  6/2006  ............ G01N 33/487
CA   2583563 Y     6/2006
(Continued)

OTHER PUBLICATIONS

FI search report of Feb. 16, 2010.

*Primary Examiner* — Peter Macchiarolo
*Assistant Examiner* — Nathaniel Kolb
(74) *Attorney, Agent, or Firm* — Seppo Laine Oy (57) ABSTRACT

The invention relates to body fluid measuring strip cartridges and apparatuses. A cartridge of the present kind comprises a body having a housing zone for a plurality of stacked test strips, a first opening on the wall of the body for bringing the test strips out of the body one at a time, and first means for sealing the first opening. According to the invention, the cartridge further comprises a second opening on the wall of the housing, the second opening allowing an external actuator to enter the housing and to move within the housing for bringing a test strip out of the body, and second means for sealing the second opening. In addition, means are arranged on said body for providing electrical connection between the reading terminals of at least one strip and external meter electronics. The invention offers a convenient way of achieving sealed storage and reading of analytical test strips for small-sized body fluid measuring apparatuses.

18 Claims, 4 Drawing Sheets

(56) References Cited

U.S. PATENT DOCUMENTS

| | | |
|---|---|---|
| 2005/0281706 A1* | 12/2005 | Funke et al. .................... 422/63 |
| 2006/0118570 A1 | 6/2006 | Fowler et al. |
| 2007/0293790 A1 | 12/2007 | Bainczyk et al. |
| 2008/0131322 A1 | 6/2008 | Kheiri |
| 2008/0267822 A1 | 10/2008 | List et al. |
| 2010/0087754 A1* | 4/2010 | Rush et al. .................... 600/583 |
| 2011/0040165 A1* | 2/2011 | Williams, III ................ 600/365 |
| 2011/0278321 A1* | 11/2011 | Chan et al. .................... 221/198 |
| 2012/0330119 A1* | 12/2012 | Shaanan et al. ............... 600/347 |
| 2012/0330189 A1* | 12/2012 | Shaanan et al. ............... 600/583 |
| 2013/0085349 A1* | 4/2013 | Shaanan et al. ............... 600/301 |
| 2013/0245392 A1* | 9/2013 | Shaanan et al. ............... 600/301 |

FOREIGN PATENT DOCUMENTS

| | | |
|---|---|---|
| CN | 1985167 A | 6/2007 |
| CN | 101065663 A | 10/2007 |
| WO | WO2006/009534 A1 | 1/2006 |
| WO | WO2006002432 Y | 1/2006 |
| WO | WO2006/044850 A1 | 4/2006 |
| WO | WO 2006044850 A | 4/2006 |

\* cited by examiner

CARTRIDGE FOR BODY FLUID MEASURING STRIPS AND A BODY FLUID MEASUREMENT DEVICE

FIELD OF THE INVENTION

The invention relates to body fluid measurement. In particular, the invention relates to a cartridge for storing a plurality of test strips suitable for analyzing body fluid, such as blood. Such cartridge is designed such that the test strips can be brought out of the cartridge for performing a body fluid measurement. The invention also relates to a body fluid measurement device containing such cartridge.

BACKGROUND OF THE INVENTION

Disposable test strips are frequently used in personal blood glucose monitors for measuring blood glucose in daily life. Test strips are typically sensitive to outside elements, in particular humidity, that may compromise measuring accuracy after long-time exposure. Therefore, during long periods of storage, the test strips must be protected from outside elements, air humidity, in particular.

Traditionally, test strips have been stored in closeable plastic vials containing, for example, 25 to 50 strips. Such vials are not easy to use as they are separate components from the meter itself, resulting in more operations and hassle needed for performing a single blood glucose measurement. An exemplary vial is disclosed in WO 03/082092.

U.S. Pat. No. 6,908,008 discloses a test device with means for storing and dispensing test strips. The test strips are stored stacked within the device and pushed out by means of a slider.

Test strips may also be stored in cartridges (also cassettes, magazines) which are filled with test strips and placed into the monitor device. Some cartridges contain means for sealing each strip individually in a separate locker of the cartridge in a foil. Such cartridges are, however, expensive and difficult to manufacture. In addition, their dimensions are relatively large because of the individual lockers, resulting in bulky integrated monitors. Thus, they are not well suitable for small blood glucose monitors designed for frequently repeated measurements in everyday life.

Examples of commercially available test strip cartridges include Bayer Ascensia Breeze and Roche Accu-Chek Compact Plus. In patent literature, stacked test trip cartridges or the like devices have been disclosed, for example, in, WO 03/042691, U.S. Pat. No. 6,908,008, EP 1314029, CA 2583563.

Another type of cartridges (in addition to individually sealed strips) are cartridges that seal all strips inside the cartridge. This cartridge type removes the need for individual sealing. Typically the strips are stored in stacks. General problems associated with sealed cartridge-type solutions for stacked strips include wearing of seals, complex mechanisms needed for closing seals and, in particular, that the mechanism for pushing out the test strips one by one is inadequately sealed. Even if the strip exit port is sealed, the device typically requires an actuator inside the cassette to push out the strips. This actuator, if operated by the device, therefore needs to enter the cassette at some location. Needless to say, such mechanism should also be hermetically sealed in order to achieve a fully sealed container.

WO 2006/044850 discloses an exemplary sealed test strip cartridge for stacked test strips. The housing of the cartridge may be sealed for inhibiting introducing moisture into the interior of the housing by a rubber seal in the opening for test strips. A rubber seal as disclosed in the publication does not, however, ensure tight sealing as such, in particular, after many repetitions of strip dispensing. In particular, the force keeping the rubber parts together, and thus sealing the cartridge, may not be sufficient or may weaken during use. The cartridge comprises an integral plunger or slide mechanism for pushing test strips out of the cartridge, significantly increasing the costs of the cartridge. Because of this, the cartridge cannot be used as a disposable cartridge. Furthermore, the publication fails to present an effective method for sealing the plunger or slide mechanism.

Further, WO 2006/002432 discloses a cartridge comprising stacked sensor strips and sealable openings on opposite sides of the cartridge for bringing the sensor strips out of the cartridge one by one. In the case of electrochemical sensor strips, the strips are read by pushing them entirely out of the cartridge and by contacting them individually with external electrical contacts arranged in a sensor-dispensing instrument. In this solution the strip will need to be pushed entirely out of the cartridge to allow its reading. This results to significant space requirements and increases the dimensions of the sensor dispensing device.

SUMMARY OF THE INVENTION

It is an aim of the invention to produce a novel cartridge for test strips which is inexpensive to manufacture and can be well sealed for storage of test strips. A particular aim is to produce a cartridge which suits well for very small portable body fluid monitors.

According to a first aspect, the cartridge comprises a body having a housing zone for a plurality of stacked test strips, a first opening on the wall of the body for bringing the test strips out of the body one at a time, and first means for sealing the first opening. According to the invention, the cartridge further comprises a second opening on the wall of the housing, the second opening allowing an external actuator, i.e., pushing member, to enter the housing and to move within the housing for pushing a test strip at least partially out of the body, and second means for sealing the second opening. The seals are designed so as to allow repeated sealing of the openings after the test strip or actuator has been removed from the opening. In particular the seals may be based on material properties, i.e. the seals comprise deformably openable and sealable passages for repeated penetration of test strips or actuator.

As the cartridge of the invention does not include an integral actuator or complex sealing mechanisms relating to them, it is more inexpensive to manufacture and small in size. When not in use, the actuator remains outside the cartridge and therefore also the second opening can remain tightly sealed. Also, in a preferred embodiment, when a strip is ejected, or actuator inserted, both openings also remain relatively sealed, as the elastic members of the openings may press tightly against the actuator or test strip. Thus, the aim of the invention is met.

It is a particular aim of the invention to produce a novel cartridge for test strips which allows for easy and robust electrical reading of the strips. This is achieved by a second aspect of the invention by providing means on the body of the cartridge for providing electrical connection between the reading terminals of at least one strip and external meter electronics while the strip is still partially inside the cartridge.

Thus, the cartridge may comprise an electrical contacting zone at said housing, which allows for contacting of external electrical reading means to be electrically contacted with reading terminals on the test strip. The electrical contacting zone is typically arranged on a wall of the cartridge which is facing the reading terminals of the test strip when it is brought partially out of the body through said first opening.

According to one embodiment, the electrical contacting zone comprises a third opening on the wall of its body, the third opening being aligned with the reading terminals of the test strip. According to a further embodiment, the third opening is designed to connect a test strip in the housing zone for the stacked test strips to a limited and airtight space within a body fluid measuring device, the electrical reading means being arranged in said space. Alternatively or in addition to that, said test strip may be arranged to be positioned against the boundaries of the third opening such that no air or moisture is conveyed to the rest of the test strips in the stack.

According to an alternative embodiment, the electrical contacting zone comprises conductors arranged through the body of the cartridge, the conductors allowing electrical connection between reading terminals of a test strip with the external reading means.

The cartridge and, in particular, any body fluid metering device using a cartridge according to this second aspect can be manufactured very compact in size, as the strip does not need to be moved entirely outside the cartridge for reading. In fact, the strip can be read while still the cartridge or such that only its measurement head (not reading terminals) is pushed out of the cartridge. The cartridge may be manufactured also at a competitive cost.

Preferably, the second opening is located on a wall of the body opposite to the first opening for allowing a test strip to be pushed out by linear motion of said external actuator. Typically, the first and second openings are aligned with each other in the direction of pushing. The second opening may be provided with essentially similar means for hermetically sealing the second opening than the first opening, making the design even more cost-effective. Said pushing may bring the test strip from a first (storage) position to a second (operation) position, in which the reading terminals of the test strip are at the electrical contacting zone of the body, i.e. aligned with the third opening or in contact with the conductors arranged through the body for allowing reading of the strip.

The body fluid measuring device according to the invention comprises a cavity for a cartridge of the above kind and an actuator for pushing test strips out of the cartridge one by one through the deformable passage into a measurement position.

The device may also comprise, a limited and airtightly sealed space comprising electrical reading means and which is adapted to be aligned with the third opening at the electrical contacting zone of the cartridge in order to facilitate reading of the test strips without exposing them to ambient air.

The second sealing means may also include components to be part in the function of pushing out the strips when activated by the external actuator.

More specifically, the invention is characterized by what is stated in the independent claims.

It is a further aim of the invention to produce a test strip cartridge which is efficiently sealed but simple to manufacture.

According to one aspect, there is provided a sealed cartridge for analytical test strips, the cartridge comprising a body having a housing zone for a plurality of stacked test strips, an opening on the wall of the housing for bringing the test strips out of the body one at a time, an elastic member having a deformable passage for a test strip and retaining means capable of attaching the elastic member to the body. In a further aspect, the attachment may be made by pressing the elastic member against the body. The cartridge may also have a second opening for entry of an actuator for pushing out strips on the opposite side of cartridge than the first opening.

Also this aspect provides significant advantages. It allows easy and secure attachment of the sealing elastic members to the cartridge body. As there is provided a constant pressing force, essentially hermetic sealing can be achieved. In addition, as the elastic member is under constant pressure, i.e. compressed, not only is the interface between the elastic member and the cartridge body sealed, but also the strip passage contained in the elastic member remains firmly sealed. It is to be noted that this aspect can be utilized independently of the first aspect, for sealing either one of the openings of the cartridge or, for example, only the strip opening of a cartridge according to prior art.

When a strip is ejected, the strip exit port also remains relatively sealed, as they press tightly against the strip.

Further advantages are obtained by means of embodiments which are the subject of other dependent claims.

According to one embodiment, the elastic member comprises two or more overlapping elastic layers, the deformable passage being formed between the overlapping layers.

According to another embodiment the deformable passage is a slit, in particular a cut in an elastic sheet.

According to a further embodiment the retaining means comprise a clip having a retaining part adapted to engage with counterpart provided at said body for achieving said pressing. The retaining part comprises a clamp adapted to engage with a recess provided on the side of the body. In a preferred embodiment, the clip comprises a face adapted to press the elastic member against the body and at least two clamps extending essentially perpendicular to said face and engaging with the body. The retaining means is preferably at least partly manufactured from resilient material so that it can be snapped on to the body of the cartridge for immobilizing the elastic member. For example, the retaining means may be a single sheet of metal folded into desired form so as to firmly engage with the body of the cartridge.

A particular aim of the invention is to achieve a novel type of sealing for cartridge, the sealing being usable both for the mechanism designed to push the test strips out of the cartridge and for dispensing the test strips.

In addition, different kinds of seals and means for their attachment may be used (known to those skilled in the art).

The cartridge may also include an opening or openings for electrical or other contacts for the device. Preferably also these openings are sealed, as will be more specifically explained later.

Still further embodiments and advantages of the invention are described in the following detailed description with reference to the attached drawings.

DETAILED DESCRIPTION OF EMBODIMENTS

Figure 1:
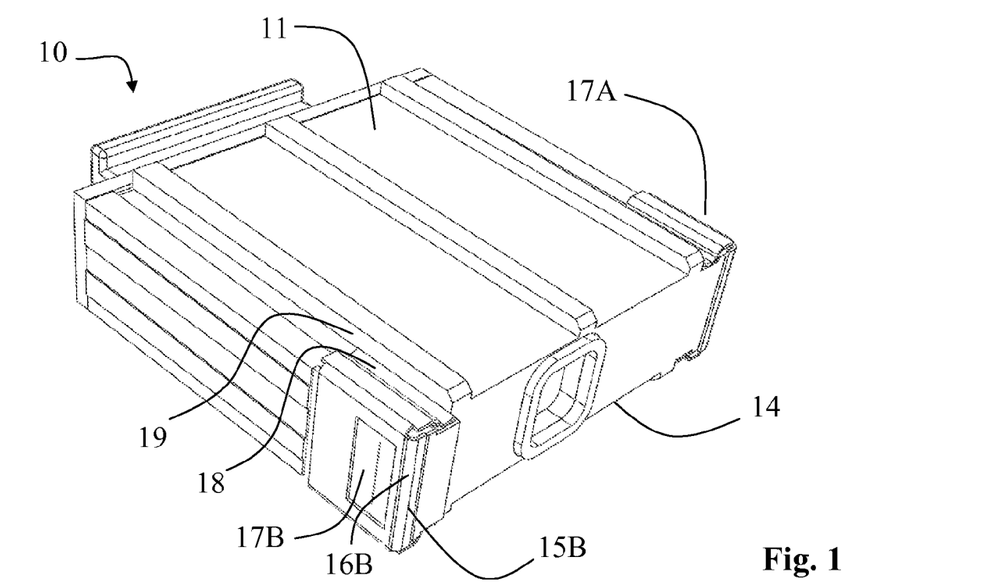
FIG. 1 shows a perspective view of a cartridge according to one embodiment of the invention.
Figure 2:
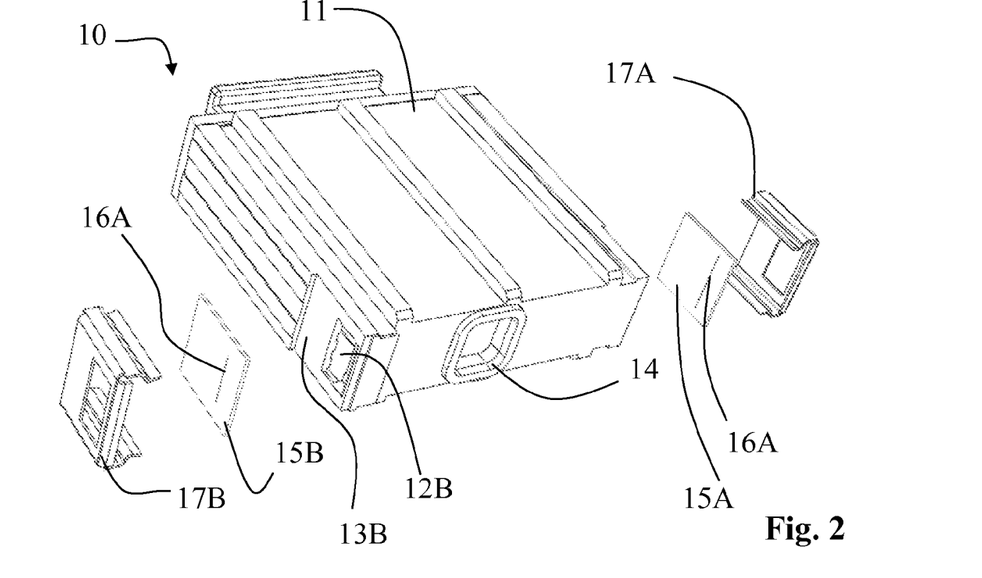
FIG. 2 shows an exploded perspective view of a cartridge according to FIG. 1.
Figure 3:
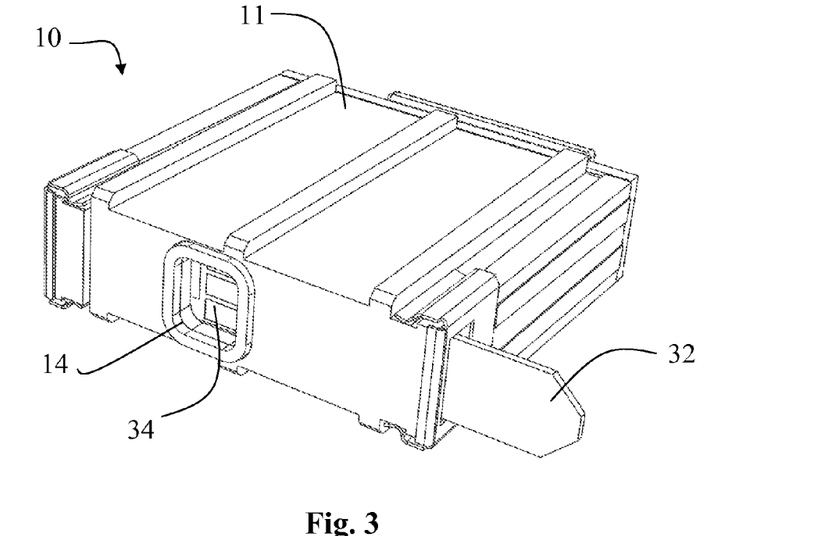
FIG. 3 shows a perspective view of a cartridge according to FIGS. 1 and 2 equipped with a test strip.

With reference to FIGS. 1-3, the cartridge 10 according to one embodiment comprises a generally rectangular body 11. On one face of the body 11, there is provided an opening 12B ("second opening") for a strip pushing member (not shown) of a monitor device, and on an opposing face another opening ("first opening", not shown in FIGS. 1 and 2) for a test strip 32. The openings are covered by elastic sheet-like members 15A, 15B, which can be tightly fitted onto respective flat zones 13B (the other fitting zone not shown) in the vicinity of the openings 12B (the other opening not shown) of the body 11. The elastic members 15A, 15B are provided with passages 16A, 16B which are normally closed but through which the test strips 32 or the pushing member can be pushed. The passages 16A, 16B are aligned with the openings 12B of the body.

Figure 4A:
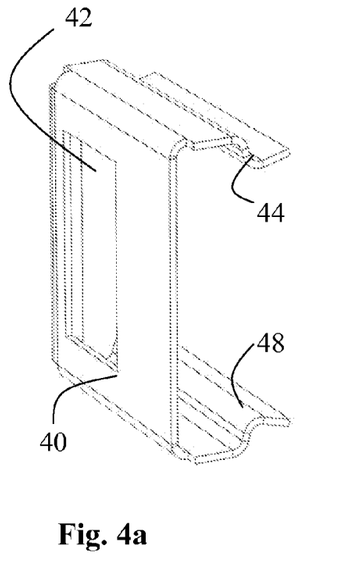
FIGS. 4a-c illustrate the retaining means for fastening the elastic sealing member to the cartridge according to one embodiment.
Figure 4B:
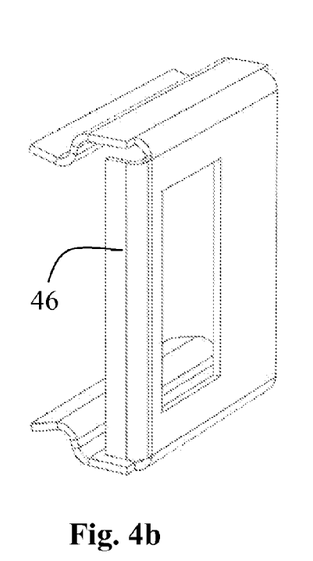
Figure 4C:
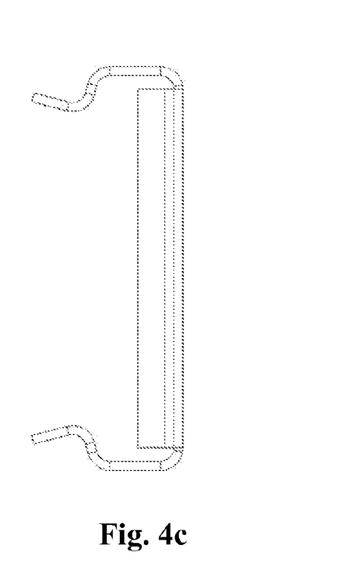

The elastic members 15A, 15B are secured to the body 11 by means of retaining means, which take the form of clips 17A, 17B. When clipped on to the body, the clips 17A, 17B press the fringe areas of the elastic members 15A, 15B against the fitting zones 13B of the body 11. With reference further to FIGS. 4a-c, the clips 17A, 17B are shaped to have resilient clamps 44, 48, which extend from the front faces 40 of the clips 17A, 17B onto the sides of the body 11. The clamps 44, 48 are shaped to have shoulders, which are directed against each other. On corresponding sides of the body 11, there are provided grooves 19, to which the shoulders of the clamps 44, 48 engage. The clamps 44, 48 are designed such that after insertion, the clips 17A, 17B press the resilient members 15A, 15B towards the body 11 for achieving efficient sealing. The clips 17A, 17B also contain an openings 42 on the front face 40 thereof, the openings 42 being aligned with the openings 12B and passages 16A, 16B and allowing the test strips 32 to exit the cartridge 10 or the pushing means to enter the cartridge. The clips 17A, 17B may also contain an additional flange 46 on a side thereof, the flange 46 serving to prevent slippage of the resilient members 15A, 15B.

The exemplary cartridge shown in FIGS. 1-3 also contains an opening 14 on the bottom face thereof. The opening 14 aids in electronic reading of the test strips 32. Thus, the test strips 32 contain reading terminals 34, which align with the opening 14 when being pushed partly out of the cartridge into a measurement position. The opening 14 may be in normal condition, i.e. when the test strip 32 is not in the measurement portion, sealed. The reading terminals 34 are exposed, for example, by the movement of the pushing means for the test strips 32. Thus, the opening 14 is preferably sealed before the cartridge is inserted into the meter but may be opened manually or automatically at insertion or during the use of the device.

The cartridge may be inserted in to a health monitoring device or other test strip dispensing device which contains a limited and substantially airtight space (not shown) to which the opening 14 communicates when the cartridge is inserted into the device. The boundary between the limited airtight space and the cartridge may comprise a gasket. Thus, even if the opening is in its open state, no ambient air can enter the cartridge. However, electrical contacting to the strips can take place through the limited airtight space and the opening. According to one embodiment, the electronic reading of test strips is carried out using conductors placed at the wall of the cartridge, thus forming an electronic pathway through the wall from the body fluid meter electronics to contact pads of the strip at measurement position. If the cartridge contains such conductors integral with the cartridge body, there are typically contact terminals provided on outer surface thereof. When inserted into the health-monitoring device or other test strip dispensing device, the contact terminals come into contact with reading means of the device.

According to one embodiment, at least one of the clips for attachment of the seals is made of a metal sheet, which is cut and folded into its final form. This embodiment allows easy and inexpensive manufacturing of well-sealed cartridges. The cut and folded metal clip is snapped onto the respective zone of the cartridge body such that the elastic member remains between them. There is no need for adhesives on either side of the elastic member, although adhesives can be used, if desired, for example for aiding the manufacturing process.

According to an alternative embodiment, at least one of the clips is made of resilient plastic providing essentially the same functionality as the metal sheet discussed above.

The body of the cartridge is preferably provided with grooves or other depressions to which the shoulders of the clamps of the clips can grab. However, as appreciated by those skilled in the art, the retaining means can be designed to be attached to the cartridge body by other means too. For example, there may be provided protrusions on the body and corresponding depressions or openings in the clips, to which the protrusions can enter for holding the retaining means.

According to one embodiment (not shown), the retaining means extend from the side of body containing the opening to be sealed to the opposing side of the body. According to a further embodiment, a retaining means manufactured as a unitary part is used to fasten the elastic members of both openings of the body.

According to one embodiment, the elastic members are made of rubber which may be natural or synthetic. According to an alternative embodiment, the elastic members are made of silicone. There are a plurality of materials available which can serve to produce the required sealing function and act as a gasket in the openings of the body when used in combination with the retaining means according to the present invention.

The elastic members are preferably rectangular but may take any desired form.

Generally speaking, the sealing function of the elastic member is at least partly based on material properties of the elastic member. That is the elastic member forms a self-sealing septum. The retaining means according to the invention further facilitate this effect by keeping the elastic member under continuous pressure. This results in that the passage of the elastic member is more efficiently sealed than in prior solutions. The elastic member as such can be implemented in various ways, some of which are described below.

Figure 5A:
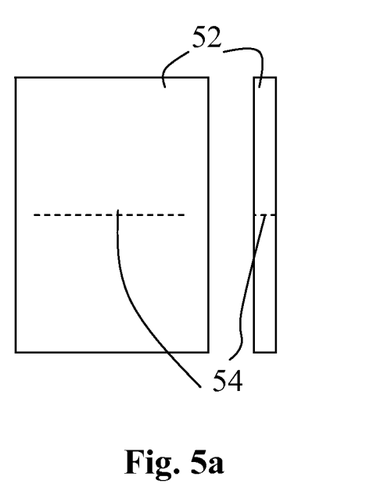
FIGS. 5a and 5b depict two embodiments of elastic sealing members.

With reference to FIG. 5a, according to one embodiment, the elastic members are manufactured from a single elastic sheet 52. The passage 54 is implemented by providing a slit, i.e. a cut, into the sheet. The elasticity and resiliency of the sheet material and/or the additional pressure applied by the retaining members, ensure that the passage 54 is in sealed condition when not in use. This embodiment has the advantages of easy and inexpensive manufacturing. According to one variation of this embodiment, there is provided two or more sheet-like elastic members which are laterally placed such that their ends form an accessible slit. The retaining members according to the invention can hold the plurality of elastic members together.

Figure 5B:
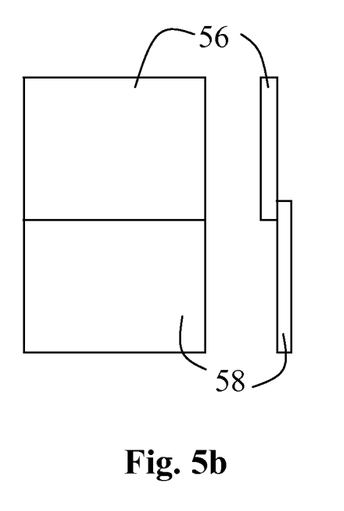

With reference to FIG. 5b, according to an alternative embodiment, the elastic members contain at least two partly overlapping layers 56, 58, which form the passage between the layers. Such arrangement can be implemented by modification or proper mutual placement of one, two or more elastic sheets. This embodiment has the advantage of even more efficient sealing of the passage due to larger possible passage channel area. Using the retaining means according to the invention, the overlapping layers remain firmly against each other in normal condition. When a test strip or a pushing member is pushed through the passage, the overlapping layers are displaced so as to form an accessible channel.

The cartridge of the above kind can be used in personal body fluid measuring devices comprising a cavity for a cartridge of the above kind and means for pushing test strips out of the cartridge one by one through the deformable passage into a measurement position. As concerns the implementation of such devices, we refer to WO 2007/010087 and WO 2008/009782 of the same applicant, the relevant contents of which are incorporated herein by reference. In particular, the relevant contents comprise the solutions relating to the casing, lancet, arrangements for bringing out of test strips and controlling of the body fluid monitor.

Figure 6A:
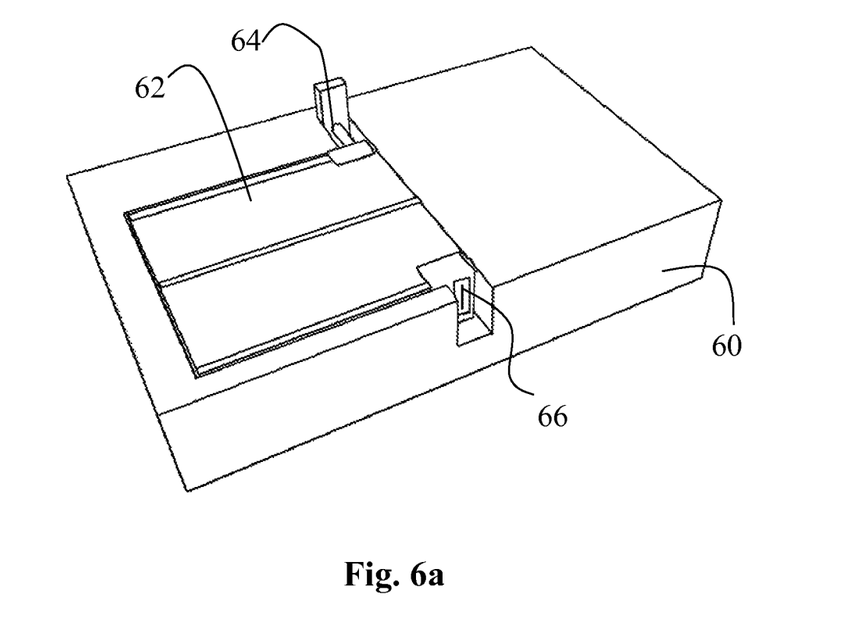
FIGS. 6a and 6b show perspective views of a measurement device according to one embodiment of the invention without and with a cover, respectively.
Figure 6B:
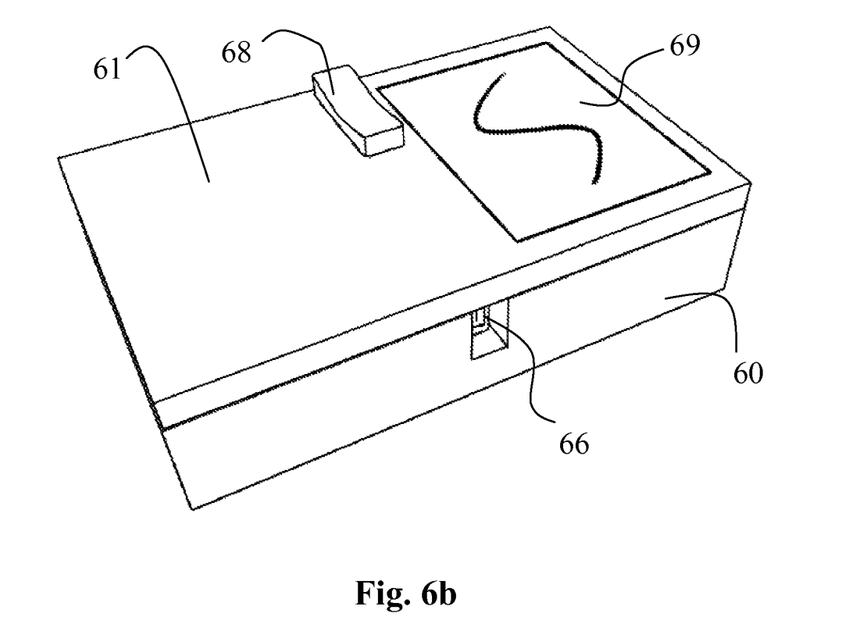

FIGS. 6a and 6b show body fluid measuring apparatus according to one embodiment. The apparatus comprises an apparatus body 60 having a space reserved for a strip cartridge 62. The apparatus comprises an actuator (plunger) 64 designed to fit from the second opening (not shown) of the cartridge 62 for engaging with a test strip and pushing the test strip out of the first opening 66. The apparatus may be provided with a second body part, i.e., a cover 61, for protecting the cartridge 62 and the actuator 64. On the surface of the body 60, there is provided interface means 68 for using the actuator 64. The actuator 64 may be spring-loaded.

According to one embodiment, means are provided at the vicinity of the second opening of the cartridge for transferring the movement of the external actuator to the test strips. That is, the actuator does not necessarily come into direct contact with the measurement strip to be pushed to measurement position but the movement may be transmitted by interface means.

The strip ejection actuator, which—when not in use—typically remains entirely outside the cassette. This arrangement enables the cartridge to be fully sealed when not in operation without complex integrated mechanism in the cassette. According to a preferred embodiment, the second opening is provided with identical sealing means, or at least operating with the same principle, than the exit opening of the strips.

Although the above detailed description frequently refers in plural form to the seals on both sides of the cartridge, the same principles can be individually applied to either one of the seals, that is, the strip exit seal or the pushing member seal. One of the openings may be sealed by some other means.

The invention claimed is:

1. A cartridge for analytical test strips, comprising
   a body having a housing zone for a plurality of stacked test strips,
   a first opening on the wall of the body for bringing the test strips out of the body one at a time,
   first means for repeatedly sealing the first opening,
   a second opening on the wall of the housing, the second opening allowing an external actuator to enter the housing and to move within the housing for bringing a test strip out of the body,
   second means for repeatedly sealing the second opening, and
   an electrical contacting zone at the housing zone for providing electrical connection between at least one test strip and external meter electronics, wherein the electrical contacting zone comprises a third opening on the side of the cartridge, through which the strip can be in contact with the external meter electronics.

2. The cartridge according to claim 1, wherein the electrical contacting zone is arranged on a wall of the cartridge facing the test strip which can be brought out of the body through said first opening.

3. The cartridge according to claim 1, wherein the third opening is sealed before the cartridge is inserted into the meter.

4. The cartridge according claim 1, wherein the second opening is located on a wall of the body opposite to the first opening for allowing a test strip to be pushed out by linear motion of said external actuator.

5. The cartridge according to claim 1, wherein at least one of the first and second means for sealing comprise an elastic member having a deformable passage for a test strip.

6. The cartridge according to claim 5, wherein at least one of the first and second means for sealing comprise two or more overlapping elastic layers, the deformable passage being formed between the overlapping layers.

7. The cartridge according to claim 5, wherein at least one of the first and second means for sealing comprising the deformable passage is a slit.

8. The cartridge according to claim 1, wherein means are provided at the second opening of the cartridge for transferring the movement of the external actuator to the test strips.

9. The cartridge according to claim 1, wherein the first and/or second means for sealing are affixed to the body by retaining means capable of pressing the elastic member against the body.

10. The cartridge according to claim 9, wherein the retaining means comprises a clip having a retaining part adapted to engage with a counterpart provided at said body for achieving said pressing.

11. The cartridge according to claim 10, wherein the retaining part comprises a clamp with a shoulder adapted to engage with a recess provided on the side of the body.

12. The cartridge according to claim 10, wherein the clip comprises a face adapted to press the elastic member against the body and at least two clamps extending essentially perpendicular to said face and engaging with the body.

13. The cartridge according to claim 10, wherein the retaining means is at least partly manufactured from resilient material.

14. The cartridge according to claim 10, wherein the retaining means comprise a single sheet of metal folded into desired form so as to firmly engage with the body of the cartridge.

15. The cartridge according to claim 1, wherein the second opening is aligned with the first opening in the direction of pushing of the test strips.

16. The cartridge according to claim 1, wherein the first and second means for sealing are essentially similar.

17. A body fluid measuring device, comprising
   a test strip cartridge having:
      a body having a housing zone for a plurality of stacked test strips,
      a first opening on the wall of the body for bringing the test strips out of the body one at a time,
      first means for repeatedly sealing the first opening,
      a second opening on the wall of the housing, the second opening allowing an external actuator to enter the housing and to move within the housing for bringing a test strip out of the body,
      second means for repeatedly sealing the second opening, and an electrical contacting zone at the housing zone for providing electrical connection between at least one test strip and external meter electronics, wherein the electrical contacting zone comprises a third opening on the side of the cartridge, through which the strip can be in contact with the external meter electronics, and an actuator adapted to move through said second opening for bringing test strips out of the cartridge one by one through the first opening into a measurement position, meter electronics for reading a measurement result from the test strip brought into the measurement position, and contacting means in functional connection with said electrical contacting zone.

18. The body fluid measuring device according to claim 17, wherein said contacting means are located in a limited substantially airtightly sealed space of the body fluid measuring device and are adapted to communicate with said electrical contacting zone.

* * * * *